United States Patent [19]
Mayenberger et al.

[11] Patent Number: 5,843,097
[45] Date of Patent: Dec. 1, 1998

[54] SURGICAL APPLICATOR

[75] Inventors: Rupert Mayenberger, Rielasingen; Pedro Morales, Tuttlingen, both of Germany

[73] Assignee: Aesculap AG, Germany

[21] Appl. No.: 792,682

[22] Filed: Jan. 29, 1997

[30] Foreign Application Priority Data

Feb. 3, 1996 [DE] Germany ............ 196 03 889.8

[51] Int. Cl.⁶ .................................. A61B 17/10
[52] U.S. Cl. .......................... 606/143; 606/142; 606/139
[58] Field of Search .................. 606/139, 142, 606/143, 144; 227/901, 902

[56] References Cited

U.S. PATENT DOCUMENTS

| | | |
|---|---|---|
| 3,463,156 | 8/1969 | McDermott . |
| 4,242,902 | 1/1981 | Green . |
| 4,549,544 | 10/1985 | Favaron . |
| 5,527,320 | 6/1996 | Carruthers et al. ........... 606/143 |
| 5,591,178 | 1/1997 | Green et al. ................. 606/143 |

*Primary Examiner*—Michael Powell Buiz
*Assistant Examiner*—Tina T. D. Pham
*Attorney, Agent, or Firm*—Barry R. Lipsitz; Ralph F. Hoppin

[57] ABSTRACT

In a surgical applicator for U-shaped clips comprising a handle, a tubular shaft adjoining the handle, a forceps-type applicator tool at the free end of the tubular shaft and a clip magazine in the tubular shaft, a closing mechanism arranged in the tubular shaft for the applicator tool, the closing mechanism being actuatable from the handle, and an advancing mechanism arranged in the tubular shaft for the clips, the advancing mechanism likewise being actuatable from the handle and pushing the clips forwards in a path of advance leading into the applicator tool, in order to prevent unintentional pushing-back of the clips in the applicator before the final application, it is proposed that a restraining nose project resiliently between the forceps-type legs of the applicator tool and into the path of advance of the clips, the restraining nose being resiliently displaced by the forwardmost clip out of the path of advance thereof when the forwardmost clip is pushed past into the applying position, and the restraining nose resiliently returning into the path of advance and resting against the rear side of the clip upon arrival of the clip in the applying position.

12 Claims, 6 Drawing Sheets

SURGICAL APPLICATOR

BACKGROUND OF THE INVENTION

The invention relates to a surgical applicator for U-shaped clips comprising a handle, a tubular shaft adjoining the handle, a forceps-type applicator tool at the free end of the tubular shaft and a clip magazine in the tubular shaft, a closing mechanism arranged in the tubular shaft for the applicator tool, the closing mechanism being actuatable from the handle, and an advancing mechanism arranged in the tubular shaft for the clips, the advancing mechanism likewise being actuatable from the handle and pushing the clips forwards in a path of advance leading into the applicator tool.

Such an applicator is known, for example, from German Utility Model G 9 413 296.8.

In such applicators in which several clips are arranged in a magazine, the clips are displaced forwards by the advancing mechanism into the applying position, the advancing mechanism is subsequently pulled back again, and the clip is then applied to the tissue structure, for example, to a blood vessel. Once the clip has been applied, it is closed by closure of the applicator tool.

With known applicator tools there is the danger that the clip arranged in the applying position will become pushed out of position in the applicator tool when applying it to the tissue structure, and difficulties may then arise when closing the clip. After the clip is pushed forward into the applying position it is not fixed therein as the advancing mechanism is retracted again after termination of the advancing procedure.

The object of the invention is to so construct a generic applicator that even when the advancing mechanism is retracted, there is no danger of the clip being pushed out of position when it is applied to the tissue structure.

SUMMARY OF THE INVENTION

This object is accomplished in accordance with the invention in an applicator tool of the kind described at the outset in that a restraining nose projects resiliently between the forceps-type legs of the applicator tool and into the path of advance of the clips, the restraining nose being resiliently displaced by the forwardmost clip out of the path of advance thereof when the forwardmost clip is pushed past into the applying position, and the restraining nose resiliently returning into the path of advance and resting against the rear side of the clip upon arrival of the clip in the applying position.

This restraining nose, which does not impede the advancing motion of the forwardmost clip into the applying position, positions itself against the rear side of the clip and then prevents the clip from being able to be pushed back in an undesired way out of the applying position in the path of advance. It is, therefore, possible to reliably fix the clip in the applying position, for example, by a front stop and by the restraining nose resting against the rear side of the clip, even when the advancing mechanism is pulled back again.

It is essential that the advancing motion of the clip is not impeded in any way as the clip itself, as it advances, pushes the restraining nose resiliently out of the path of advance, and, after the clip has passed, the restraining nose returns resiliently by itself into the position in which it projects into the path of advance and in which the clip is secured against being pushed back.

In accordance with a preferred embodiment, it is, furthermore, advantageous for the restraining nose to have slide surfaces or edges at the sides thereof and for the forceps-type legs to rest against these slide surfaces or edges during the closing motion of the applicator tool and thereby resiliently displace the restraining nose out of the path of advance of the clip. On the one hand, it is thereby ensured that the restraining nose which projects between the forceps-type legs will not impede their closing motion. On the other hand, when closing the forceps-type legs and hence when drawing together the clip, the restraining nose is removed from the position in which it rests against the clip and, therefore, rearward motion of the central area of the clip is made possible. Such rearward motion can occur during the deformation of the clip. When drawing together the forceps-type legs of the applicator tool, the legs of the clip are also drawn towards each other, and the bridge joining the two legs of the clip can be deformed such that it is bent rearwardly to a slight extent. Owing to the restraining nose being lifted out by the closing motion of the forceps-type legs, the possibility of such rearward motion of the clip being impeded by the restraining nose projecting into the path of advance is excluded.

Provision may be made for the restraining nose to be resiliently mounted at the forwardmost end of the tubular shaft.

In a particularly preferred embodiment in which the clip magazine is insertable in the tubular shaft, provision may be made for the restraining nose to be resiliently mounted on the clip magazine.

Herein, it is, in particular, expedient for the restraining nose to be integrally formed on an outer wall of the clip magazine.

The restraining nose may be joined to the outer wall of the clip magazine via an elastically deformable region, the material of which is weakened, so the resilient motion of the restraining nose occurs through this region of weakened material, but the restraining nose itself remains essentially undeformed.

The restraining nose preferably consists of plastic, in particular, of a sterilizable plastic.

The following description of preferred embodiments of the invention serves in conjunction with the drawings to explain the invention in greater detail.

DETAILED DESCRIPTION OF THE INVENTION

The applicator illustrated in the drawings comprises a handle 1 and a tubular shaft 2 rotatable about its longitudinal axis and releasably held on the handle 1. The outer diameter of the tubular shaft 2 is slight in comparison with its length. For example, the length can be 25 cm, the outer diameter 10 mm. Two jaws 4 of a forceps-type applicator tool are mounted at the free end of the tubular shaft 2 for swivel movement about a common swivel axis 3. These can be opened and closed from the handle 1 via a closing mechanism arranged in the interior of the tubular shaft. For this purpose, the handle 1 is rigidly connected to a first handle part 5, relative to which a second handle part 6 is mounted for swivel movement on the handle 1. This second handle part 6 is articulatedly connected to a push-and-pull rod in the form of a sleeve 7 which extends through the entire tubular shaft 2 as far as the closing mechanism 8. By swivelling the handle parts 5 and 6 relative to each other, the jaws 4 of the applicator tool can be opened and closed, as is known in tubular shaft instruments.

Immediately adjacent to the applicator tool formed by the jaws 4, the tubular shaft 2 has an opening 9 extending over the front part of the tubular shaft. The opening 9 extends over approximately 180° in the circumferential direction so that in the region of this opening 9, the tubular shaft 2 is only closed in the lower half of the tubular shaft by a lower shell 10, but is open on the upper side.

The opening 9 on the upper side of the tubular shaft 2 can be closed by a clip magazine 11 inserted in this opening 9. The clip magazine 11 has essentially an almost semicircular cross section and supplements the cross section of the tubular shaft 2 to form a complete circle. This clip magazine 11 has on its side near the handle a projection 12 which immediately adjacent to the opening 9 projects slightly into the tubular shaft 2 and thereby engages under the edge delimiting the opening 9. At the front part, two walls or lugs 13 are formed at the sides on the clip magazine 11. These engage complementary recesses in the lower shell 10 and in the assembled state snap with inwardly projecting end regions into corresponding grooves 15 of the lower shell 10, i.e., in this region there is an elastic locking of the lugs 13 with the side walls of the lower shell 10. By inserting the projection 12 into the tubular shaft 2 and by this locking connection, the clip magazine 11 is fixed in a stable manner on the tubular shaft 2, but this connection is releasable again as the snap connection can be released again by forcibly pulling the clip magazine off the lower shell 10.

The tubular shaft 2 projects into a grip sleeve 23 which is displaceable in the longitudinal direction against the action of a spring 22 on the handle 1. The grip sleeve 23 is part of a ball-type locking mechanism connecting the tubular shaft 2 to the handle 1. This grip sleeve 23, mounted for displacement in the longitudinal direction on the handle 1, fixes in a radially inward position several spherical locking bodies 24 displaceable into radial openings in the handle when the spring 22 is relaxed. It does, however, allow radial outward movement of this locking body 24 when the grip sleeve 23 is pulled back against the action of the spring 22. In the radially inwardly pushed position, the locking members 24 enter radial recesses 25 of the tubular shaft 2 and fix it in the axial direction on the handle, however, in their radially outwardly displaced position, the locking members 24 release the tubular shaft 2 so it can be pulled in the axial direction out of the handle 1.

The sleeve 7 arranged in the tubular shaft 2 passes through the connection point between tubular shaft 2 and handle 1 into the handle 1 and is articulately connected there to the handle part 6 via two side pins 28 which engage openings 29 which are open at the sides. When the handle part 6 is swivelled relative to the handle part 5, the sleeve 7 is thereby pushed forwards and backwards.

Figure 3:
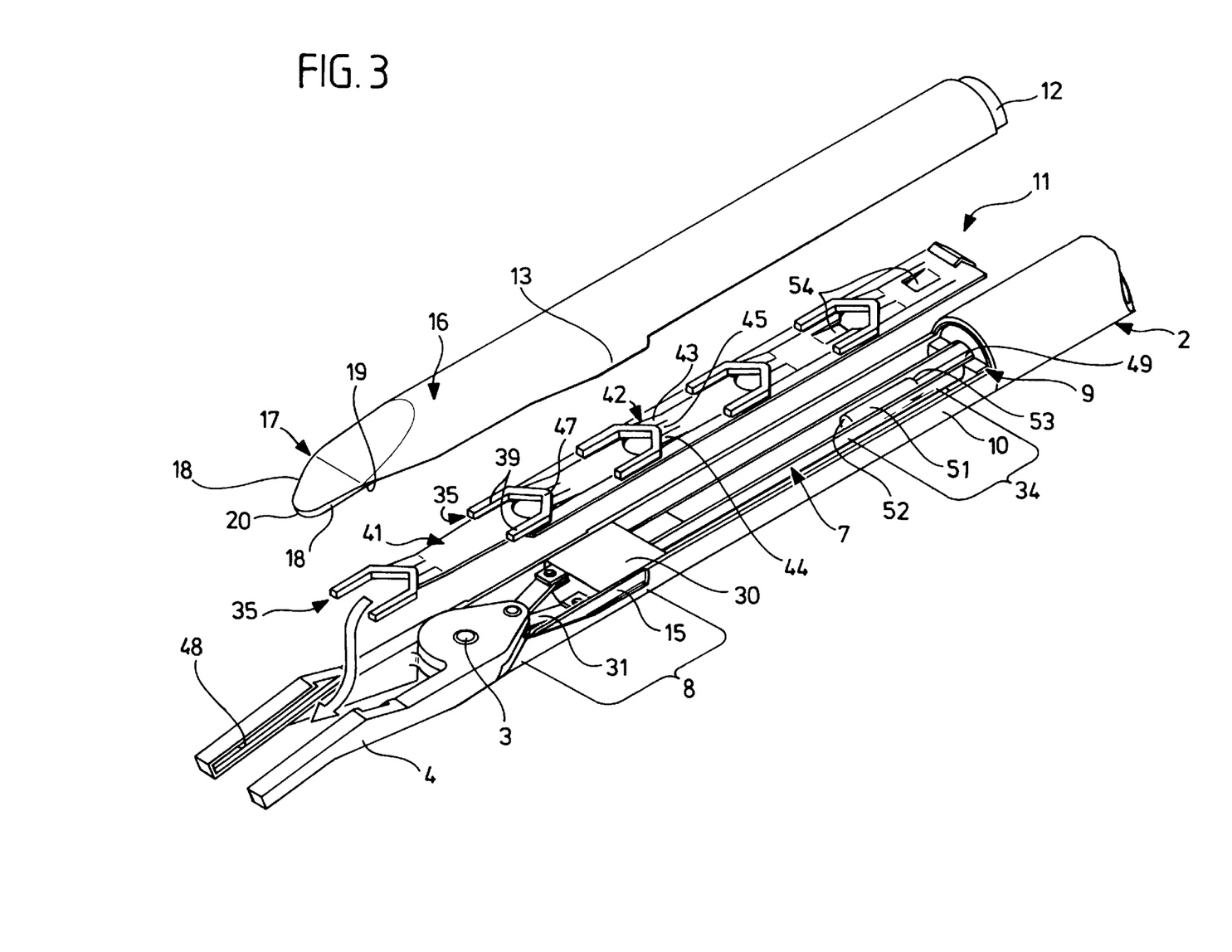
FIG. 3 a perspective view of the front part of the tubular shaft instrument of FIG. 1 in an exploded illustration.
Figure 4:
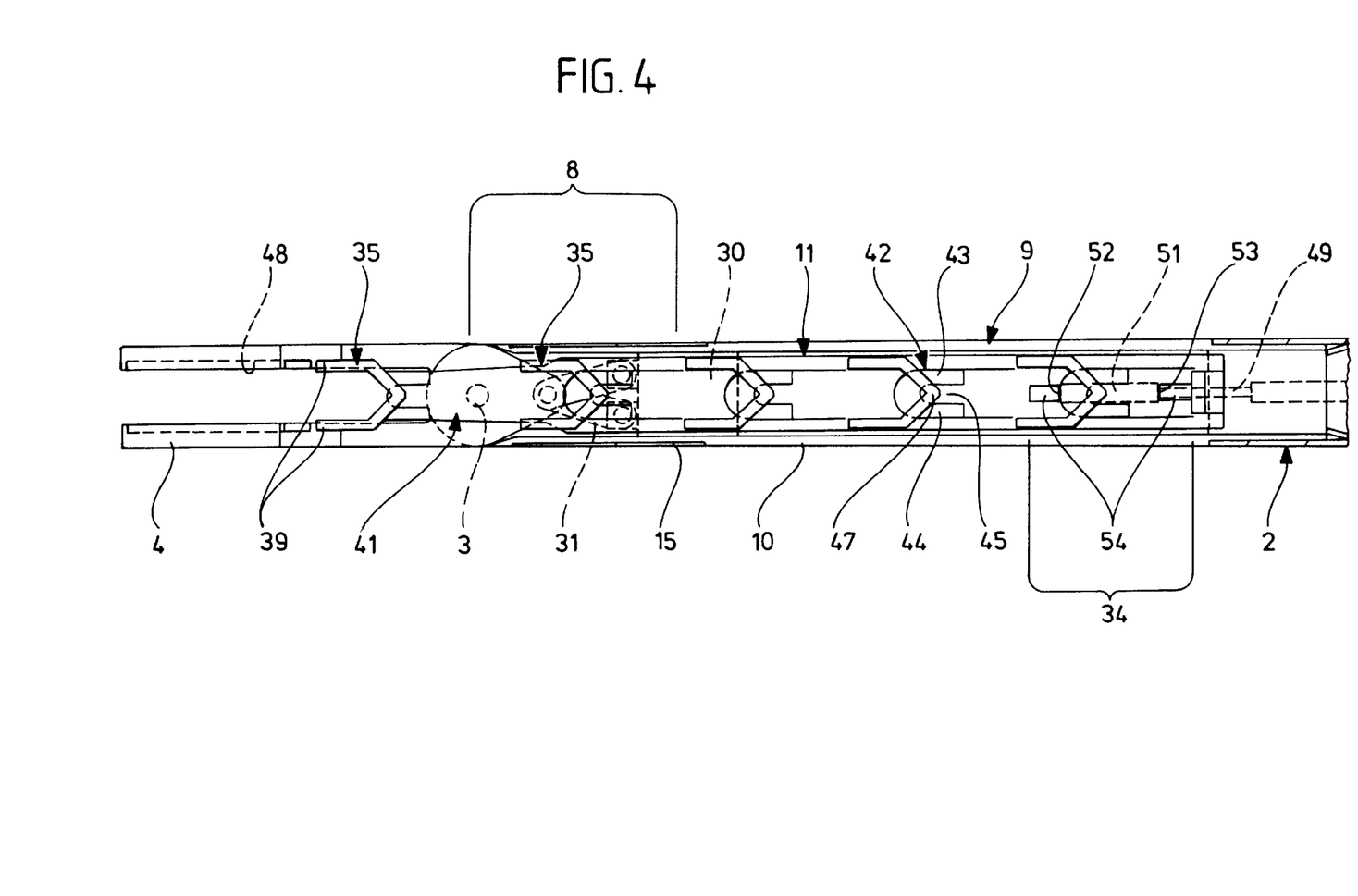
FIG. 4 a plan view of the front part of the tubular shaft instrument of FIG. 1 without the outer wall of the clip magazine and without the resilient restraining nose.
Figure 5:
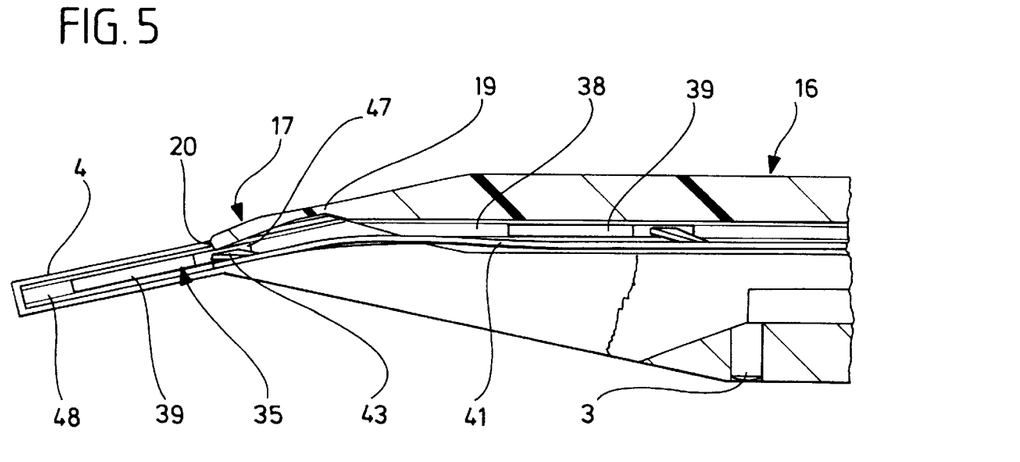
FIG. 5 a longitudinal sectional view of the forwardmost part of the applicator tool of FIG. 1 when pushing a clip past the elastic restraining nose.
Figure 6:
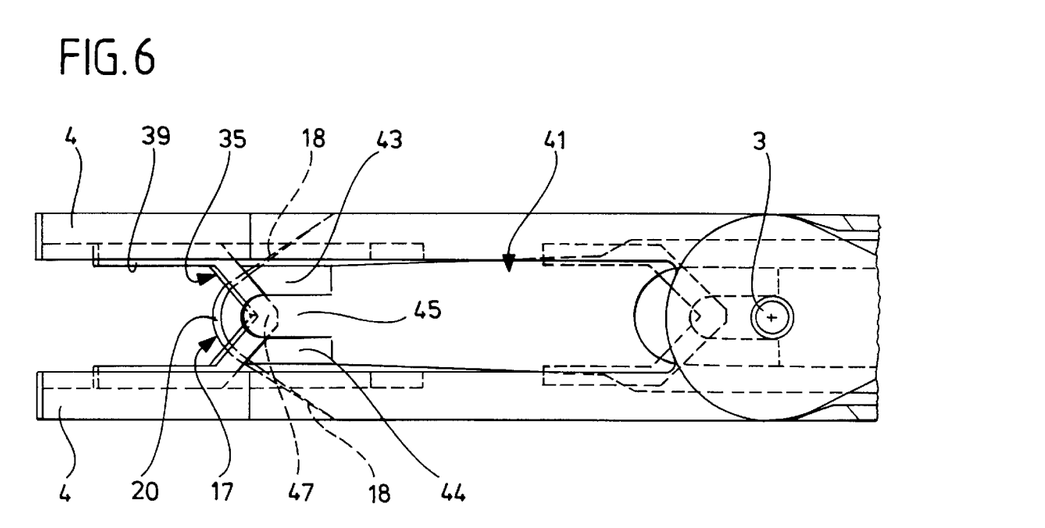
FIG. 6 a view of the applicator of FIG. 5 from below.
Figure 7:
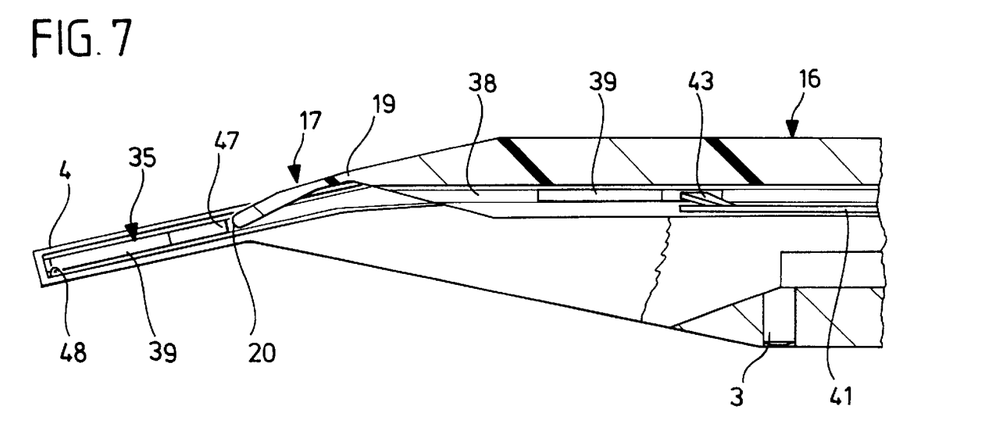
FIG. 7 a view similar to FIG. 5 with the clip in the applying position, the applicator tool open and the restraining nose lowered.

In the region of the opening 9 of the tubular shaft 2, the sleeve 7 is cut open in the upward direction so that it forms in this region only a lower shell which at its free end is firmly connected to a slide block 30 which is mounted for longitudinal displacement in the lower shell 10 and thereby fills out the cross section of the lower shell 10. This slide block 30 is articulately connected to one respective jaw 4 of the applicator tool via one respective connecting lever 31 so that one respective jaw 4 and one connecting lever 31 form a toggle lever (FIG. 3). By pushing the slide block 30 forwards and backwards, this toggle lever can be bent to a greater or lesser extent, thus bringing about swivel movement of the jaws 4. The arrangement and dimensions are chosen such that, for example, on pushing the slide block forward, the toggle lever is bent to a greater extent, more specifically, preferably to the extent that it forms almost a right angle between the connecting lever 31 and the jaw 4 when the jaws 4 are completely closed. As a result of this, a maximum torque can be exerted on the jaws 4 and so a strong closing force is generated. When the slide block 30 is pulled back, the jaws 4 are opened again. This opening is promoted by a helical spring 32 which surrounds the sleeve 7 coaxially and is supported at one end on a projection of the lower shell 10 and at the other end on a ring shoulder 33 which is permanently connected to the sleeve 7. The sleeve 7 is thereby acted upon in the direction towards the handle 1 with a spring force which supports the opening of the jaws 4.

The closing mechanism 8 comprising the slide block 30, the connecting lever 31 and the rearward part of the jaws 4 is fully accommodated in the lower shell 10 and thus leaves the entire opening 9 free to receive an advancing mechanism 34 for the clips 35 and to receive the clip magazine 11 containing the clips 35.

Located in the clip magazine 11 is a downwardly open receiving chamber 36 for the clips 35 which has the shape of a longitudinal groove in the clip magazine 11. Machined in the side walls of this receiving chamber 36 are guide grooves 38 which are arranged opposite each other and into which the legs 39 of the U-shaped clips 35 extend. Several of these U-shaped clips 35 are arranged in this way one behind the other in the receiving chamber 36 and thereby maintain a spacing relative to one another (FIG. 3).

Further guide grooves extend in the side walls parallel to the guide grooves 38. A flat or plate-shaped holder 41 which closes the receiving chamber 36 in the downward direction and extends over the entire length of the clip magazine 11 is arranged for longitudinal displacement in these further guide grooves.

The holder 41 has in the longitudinal direction several punched-out spring tongues which are each divided at their front end by longitudinal cuts into three spring tongues 43, 44 and 45 arranged alongside one another. The two outer spring tongues 43 and 44 are bent obliquely towards the receiving chamber 36 in the region of their free end and so the free edges extend obliquely to the surface of the holder 41 and project upwardly over this surface towards the receiving chamber 36.

When the holder 41 is located in its pulled back position, these edges each rest against the bridge 47 of a clip 35 joining the two legs 39, and the obliquely extending edges ensure that even if the contour of the bridge 47 is line-shaped, the edges rest securely thereagainst and are prevented from sliding off. The center spring tongue 45 of the spring tongue 42 positions itself against the underside of the clips and in this way also reliably prevents the edges from sliding over the clips on the upper side.

When the holder 41 is pushed forwards, each pair of spring tongues 43, 44 thus takes a clip 35 along with it and pushes this clip 35 in the clip magazine 11 forwards by the amount of the displacement of the holder 41.

The forwardmost clip 35 is thereby pushed forwards out of the guide grooves 38 in the side walls of the receiving chamber 36 and moves into guide grooves 48 adjacent to and in alignment with the guide grooves 38 on the inner sides of the jaws 4.

At its front end, the holder 41 terminates in a spring tongue 42 which, in all, is narrower than the holder 41. When the holder 41 is pushed forward, this spring tongue 42 moves in between the jaws 4 and pushes the clip 35 into the somewhat downwardly inclined grooves 48 of the jaws 4 as far as their front end. Owing to the narrow resilient design of the spring tongue 42 in the front part, it can readily follow the somewhat changed inclination of the guide grooves 48.

The clip magazine 11 essentially consists of an upper, cover-like half shell 16 into which the clips 35 and the holder 41 are inserted in the described manner. For reasons of clarity, these parts are separated from one another in FIG. 3.

At its front end adjacent to the jaws 4, the half shell 16 carries a resilient restraining nose 17 in the form of an essentially triangular plate rounded off at the front end with two side edges 18 extending obliquely towards each other. This restraining nose 17 is integrally connected to the half shell 16 via a flexible region 19, the material of which is of reduced thickness. This component is preferably made of sterilizable plastic by, for example, an injection process.

Owing to the flexible region 19, the material of which is reduced in thickness, the plate-shaped restraining nose 17 is elastically bendable relative to the half shell 16 about a swivel axis extending transversely to the longitudinal direction thereof.

In the undeformed state, the restraining nose 17 projects downwards to a slight extent and thus enters the space between the two jaws 4, more specifically, to such a depth that the rounded-off front edge 20 of the restraining nose 17 projects into the path of advance of the clips 35 which is defined by the guide grooves 48 in the jaws 4. This front edge 20 is set back from the front end of the jaws 4 by a distance which corresponds essentially to the undeformed clip 35.

When the holder 41 pushes the forwardmost clip 35 into the forwardmost position, the so-called applying position, the bridge 47 of the clip 35 pushes the restraining nose 17 projecting into the path of advance elastically out of the path of advance so the clip 35 can readily slide past the restraining nose 17 until it has reached the applying position. At this moment, the restraining nose 17 bent elastically out of the path of advance by the clip 35 can project into the path of advance again under the action of its inherent elasticity, and the front edge 20 of the restraining nose 17 then positions itself in the region of the bridge 47 against the rear end of the clip 35 in the applying position so that when the holder 41 is subsequently retracted, the clip is held in the applying position and secured against being pushed back. This also applies when the clip is applied to the tissue site. Even if the tissue presses against the clip, the clip is not pushed backwards in the applicator tool.

Figure 8:
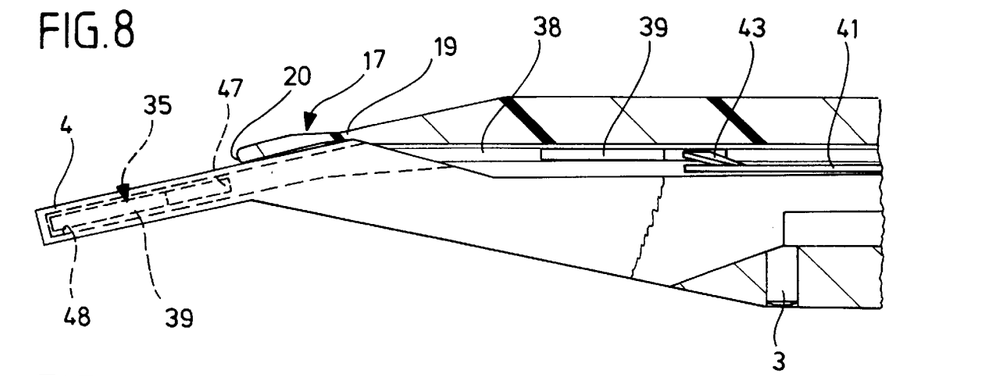
FIG. 8 a view similar to FIG. 7 with the applicator tool closed and the restraining nose elastically raised.
Figure 9:
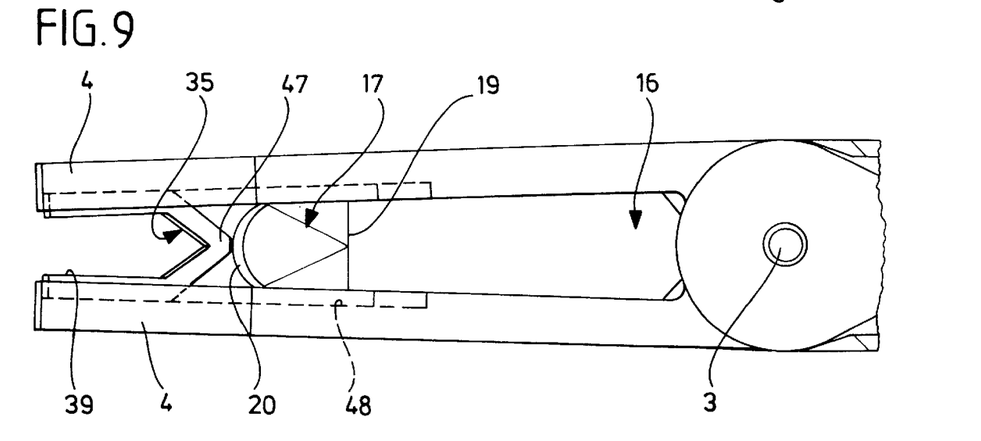
FIG. 9 a view of the applicator of FIG. 8 from below.

When closing the jaws 4, these position themselves against the oblique side edges 18 of the restraining nose 17 and press it during the further closing out of the path of advance. The restraining nose 17 is thereby bent upwards elastically, as illustrated in FIGS. 8 and 9. The fixing of the clip 35 in the applying position is thereby terminated, and the bridge 47 of the clip can now also move rearwardly owing to the deformation during the closing without being prevented therefrom by the restraining nose 17 projecting into the path of advance.

During the rearward movement of the holder 41, the spring tongues 42 slide along the following clips 35 until they stand fully behind these again and can spring upwards again into the take-along position in which the edges rest against the bridges 47 of the clips 35. If there is no clip 35 in part of the clip magazine 11, the spring tongues 43 and 44 then slide along the bottom of the receiving chamber 36 without taking a clip along, and the movement of the holder 41 is in no way hindered thereby.

It will thus be apparent that merely by forward and rearward movement of the holder 41, one clip 35 at a time can be pushed successively in between the jaws 4 and then applied in the described manner by closing the jaws in order, for example, to occlude a blood vessel.

This is carried out until the clip magazine 11 is empty, whereupon a new clip magazine 11 can be inserted in a simple way to replace the empty one, and the procedure is then continued.

Figure 1:
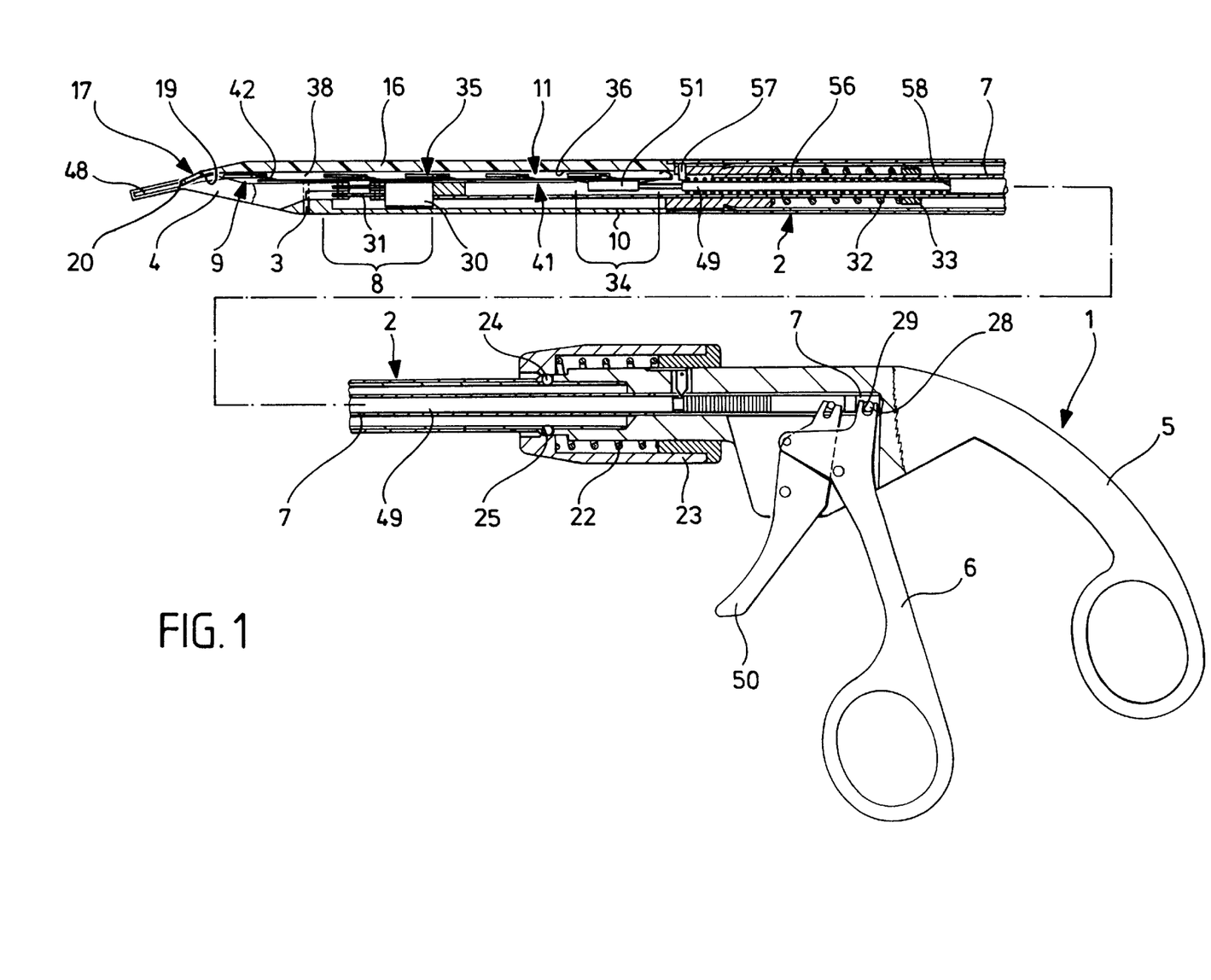
FIG. 1 a longitudinal sectional view of a surgical applicator in the form of a tubular shaft instrument.
Figure 2:
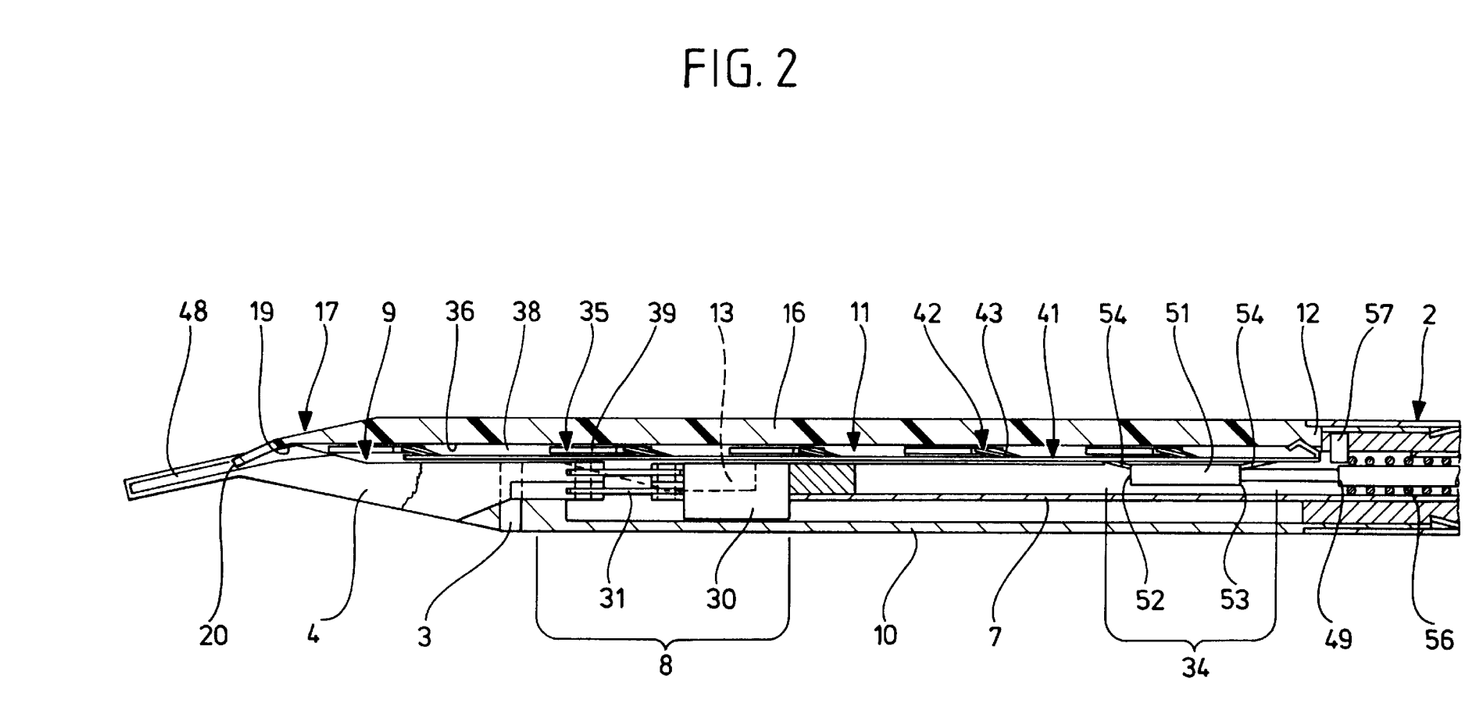
FIG. 2 a longitudinal sectional view of the front tubular shaft part of the applicator of FIG. 1.

The holder 41 is displaced by the advancing mechanism 34. which can be of very simple design. In accordance with the illustrations of FIGS. 1 and 2, it comprises a push-and-pull rod 49 guided for longitudinal displacement in the interior of the sleeve 7 and articulately connected to a swivel lever 50 on the handle 1. The swivel movement of the swivel lever 50 causes the push-and-pull rod 49 to be displaced within the tubular shaft and within the sleeve 7. At its free end, the push-and-pull rod 49 carries a driver 51 with a front and a rear contact surface 52 and 53, respectively, extending perpendicularly to the direction of displacement. Spring tongues 54 extending from the holder 41 in the direction opposite thereto and projecting downwardly rest with their edges against the contact surfaces 52 and 53.

Use of these spring tongues 54 makes it possible to bring the driver 51 into engagement with the holder 41 after insertion of a clip magazine 11 simply by the driver being displaced in the longitudinal direction. It then slides on the spring tongues 54 until it reaches the take-along position, and the edges of the spring tongues 54 hold it in this position in both directions.

The push-and-pull rod 49 is concentrically surrounded by a helical spring 56 which is supported, on the one hand, at a projection 57 of the tubular shaft 2 and, on the other hand, at a step 58 of the push-and-pull rod 49 and thereby displaces the latter into the retracted position. Forward displacement of the holder 41 in the direction towards the free end of the tubular shaft 2 thus occurs against the action of the helical spring 56 which is located inside the sleeve 7.

What is claimed is:

1. A surgical applicator for generally U-shaped clips, comprising:

a tubular shaft with a control end and an opposing free end;

a handle disposed at said control end;

a forceps-type applicator tool at said free end;

a clip magazine in said tubular shaft;

a closing mechanism arranged in said tubular shaft for said applicator tool, said closing mechanism being actuatable from said handle;

an advancing mechanism for clips carried by said clip magazine in said tubular shaft, said advancing mechanism being actuatable from said handle and pushing said clips forward in a path of advance leading into said applicator tool; and a restraining nose projecting resiliently between forceps-type legs of said applicator tool and into said path of advance of said clips; wherein:

said restraining nose is resiliently displaced by a forwardmost clip out of the path of advance thereof when said forwardmost clip is pushed past the restraining nose into an applying position;

said restraining nose resiliently returns into said path of advance and rests against a rear side of said clip upon arrival of said clip into said applying positions;

said restraining nose is resiliently carried by said clip magazine; and said restraining nose is integrally formed on an outer wall of said clip magazine which also forms an outer wall of said tubular shaft.

2. An applicator as defined in claim 1, wherein said restraining nose has slide surfaces or edges at the sides thereof, against which slide surfaces or edges of said forceps-type legs rest during a closing motion of said applicator tool and thereby resiliently displace said restraining nose out of said path of advance of said clip.

3. An applicator as defined in claim 1, wherein said restraining nose is resiliently carried at a front end of said tubular shaft.

4. An applicator as defined in claim 1, wherein said restraining nose is joined to said outer wall of said clip magazine via an elastically deformable region, the material of which is weakened.

5. An applicator as defined in claim 1, wherein said restraining nose consists of plastic.

6. A surgical applicator as defined in claim 1, wherein: said closing mechanism is a push-pull mechanism.

7. A surgical applicator as defined in claim 1, wherein: said restraining nose is substantially immovable in a direction of said path of advance.

8. A surgical clip applicator, comprising:

an elongated shaft with opposing forceps legs mounted at a front end thereof for swivel movement about a swivel axis, control handle means mounted at an opposing rear end of said shaft, and a first push-pull control member extending through said shaft to allow said control handle means to actuate said forceps legs;

said shaft having an opening which extends over a front portion thereof for receiving a clip magazine;

said clip magazine comprising a holder for holding clips, and a cover for covering said clips and said opening of said shaft;

said holder being longitudinally displaceable in said shaft;

a second push-pull control member extending through said shaft to allow said control handle means to longitudinally displace said holder to pushing a forwardmost clip of said holder forward in a path of advance leading into said forceps legs;

said forceps legs comprising slide surfaces for receiving said forwardmost clip in an applying position; and a restraining nose projecting resiliently from said cover between said forceps legs and into said path of advance such that:

said restraining nose is resiliently displaced by said forwardmost clip out of the path of advance when said forwardmost clip is pushed past the restraining nose into said applying position; and upon arrival of said clip into said applying position, said restraining nose resiliently returns into said path of advance and rests against a rear side of said forwardmost clip, and said forceps jaws are adapted to be actuated by said control handle means to crimp the forwardmost clip.

9. An applicator as defined in of claim 8, wherein:

said control handle means allow independent operation of said first and second push-pull members.

10. An applicator as defined in claim 8, wherein:

said clip magazine is adapted to be received by said opening via a snap connection.

11. An applicator as defined in claim 8, wherein:

said holder comprises first and second spring tongues projecting therefrom;

said second push-pull member comprises a push pull rod coupled to a driver; and said driver has front and rear contact surfaces for engaging said first and second spring tongues, respectively, to allow said control handle means to longitudinally displace said holder within said shaft.

12. An applicator as defined in claim 8, wherein:

said restraining nose is substantially immovable in a direction of said path of advance.

\* \* \* \* \*